Jan. 10, 1933. J. A. MASON Plant Pat. 52

ROSE

Filed Oct. 10, 1931

INVENTOR
JOHN A. MASON
BY Miller Boyken & Breed
ATTORNEYS

Patented Jan. 10, 1933

Plant Pat. 52

UNITED STATES PATENT OFFICE

JOHN A. MASON, OF BURLINGAME, CALIFORNIA

ROSE

Application filed October 10, 1931. Serial No. 568,043.

This invention relates to roses, and the object of the invention is to produce a rose of unusual beauty both in color as well as in form.

Figure 1:
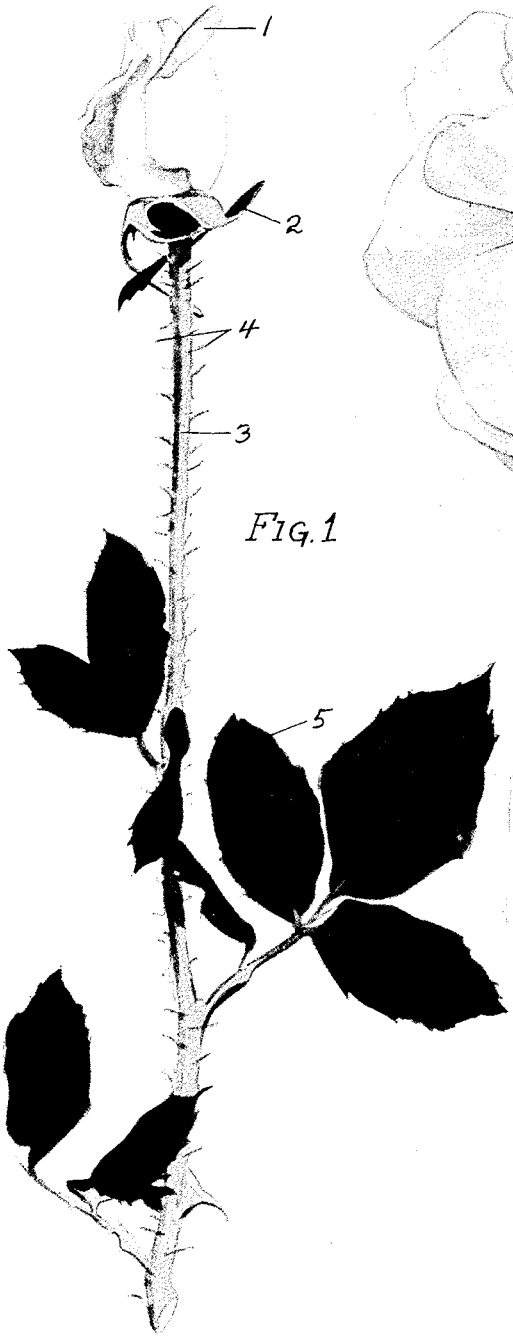
Figure 2:
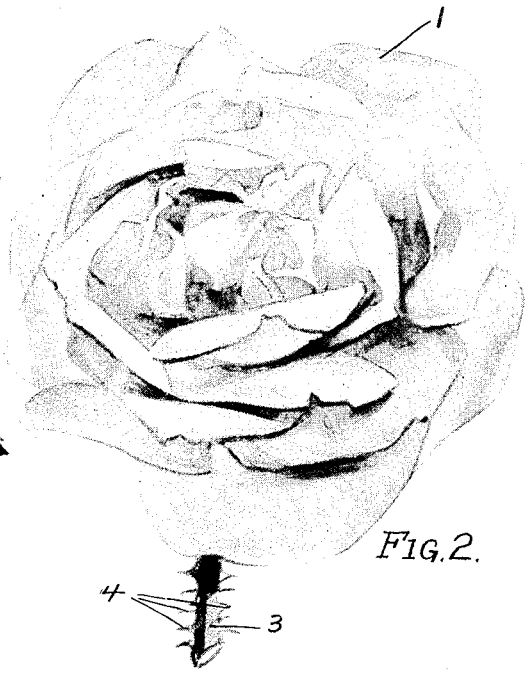

In the drawings accompanying this application my improved rose is shown. Fig. 1 is a full size view of stem, leaves and bud. Fig. 2 is my rose fully developed, and Fig. 3 a fully opened flower exposing the center, stamens, etc.

This rose was developed after several years experimenting with cross-pollination between a Dreux and a Premier rose, the pollen of the former were dusted onto the stigma of the latter, the seeds of this flower were collected and planted, and after repetition of this work and the raising of many thousands of plants to maturity, a plant was finally produced having the characteristics herein described, and this was grafted both to a wild rose and to a Russell with equal success.

This rose is very large and may be grown both in and out of greenhouses from slips or grafts. The rose is free of mildew and "blackspot". The flowers may be cut when tight buds and will develop and open up perfectly.

The color of the rose is unusual, not heretofore seen in roses, and its fragrance is rich and lasting.

The petals 1 are characterized by ranging from light madder carmine on outermost rows through light purple lake at middle rows to light carmine at center. The petals each merge into an alizarin yellow at their bases the yellow extending toward the center of each petal to be visible when the rose is in full bloom and with a rather well-defined line of demarcation as at 1′ in Fig. 3.

In the bud, the underside of the outermost row of petals, being the only visible portion, is alizarin yellow tending to orange at the base and merges into a carmine at the outer or upper half of the petals, the yellow and carmine being deeper in tint than when the rose opens.

The calyx 2 has a long leaf-like tip fringed with reddish tint.

The stem 3 is relatively thick and sturdy and from about 5 to 8 inches in length from the flower to the leaves, and is thickly covered with fine thorns 4 which are generally so very flexible at the points that the stem may be handled with little or no inconvenience. The color of the stem most nearly approaches a middle tint of "Hooker's green #1".

The leaves 5 are similar to the leaves of the wild rose, being of a somewhat rubbery texture, glossy on the upper surface and very dark in color on the upper surface, being a greenish bronze tending toward black. The underside of the leaves are of an olive green color and finely veined with darker green.

When the rose is in full bloom, several days before dropping the petals, the pistil 6 and stamens 7 are clearly visible giving the appearance of a very large wild rose, except that the rose is double and not single, having four to five rows of petals. The diameter of the flower when in full bloom is about five inches, and some grow appreciably larger.

Figure 3:
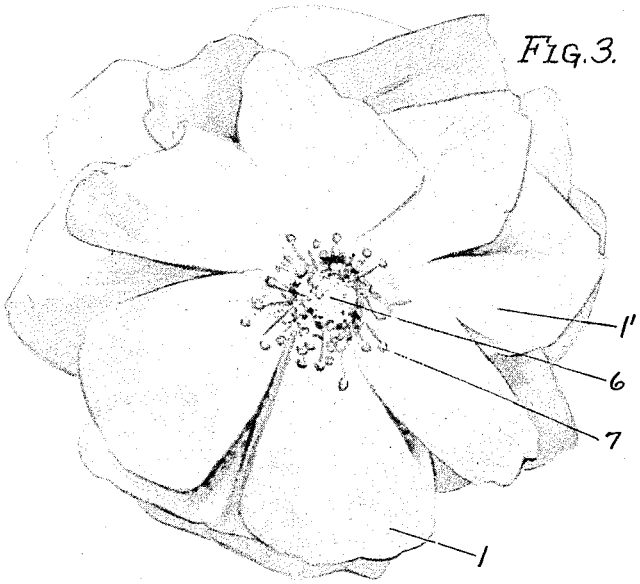

The pistil and stamens in the center of the blossom define a circle of about 1 inch in diameter in a full size flower, the stamens having reddish filaments, which, with the yellow pollen-bearing ends or anthers gives an orange appearance to the center. This size of the central group of organs is caused to appear larger when the flower is fully open by the yellowish central portions 1′ of the petals as shown in Fig. 3.

The colors referred to above are taken from the standard publication by Windsor & Newton Ltd. London 1924 Edition, "Specimen Tints of Artists Colours" in which the color charts are given.

| | |
|---|---|
| Alizarin yellow | Page 16, Plate 5, Class 2, Series 2. |
| Carmine | Page 16, Plate 6, Class 3, Series 4. |
| Madder carmine | Page 12, Plate 4, Class 1, Division 2, Series 2. |
| Madder lake | Page 16, Plate 3, Class 1, Division 2, Series 4. |
| Purple lake | Page 16, Plate 6, Class 3, Series 2. |
| Bronze | Page 16, Plate 6, Class 3, Series 1. |
| Hooker's green #1 | Page 16, Plate 5, Class 2, Series 1. |

Having thus described my improved rose, I claim:—

A rose substantially as shown and described and characterized by a flower supported on a relatively heavy stem having relatively soft thorns and foliage of a deep green color tending toward black, which flower has a plurality of rows of petals which open after the manner of a wild rose, that portion of the inner row of petals adjacent the stamens being yellow in color and which color merges outwardly into a light carmine color, and the outside of the outer row of petals being yellow merged into orange color adjacent the base of the petals and merging outwardly into a light carmine color.

JOHN A. MASON.